(12) United States Patent
Burns et al.

(10) Patent No.: US 6,989,240 B2
(45) Date of Patent: Jan. 24, 2006

(54) METHOD FOR DETECTING HEMOLYSIS

(75) Inventors: Edward R. Burns, Fresh Meadow, NY (US); Vadiraja Murthy, Teaneck, NJ (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 277 days.

(21) Appl. No.: 08/746,635

(22) Filed: Nov. 13, 1996

(65) Prior Publication Data

US 2002/0012952 A1    Jan. 31, 2002

Related U.S. Application Data

(63) Continuation of application No. 08/421,079, filed on Apr. 13, 1995, now abandoned.

(51) Int. Cl.
*G01N 33/53*    (2006.01)
(52) U.S. Cl. ..................... 435/7.25; 435/7.4; 435/7.9; 435/15; 435/963; 436/506; 436/518; 436/530; 436/531; 436/539; 436/542; 436/548; 436/63; 436/804; 436/811
(58) Field of Classification Search ............... 435/7.25, 435/7.4, 7.9, 15, 973, 963; 436/506, 518, 436/530, 531, 539, 542, 548, 63, 804, 811
See application file for complete search history.

(56) References Cited

U.S. PATENT DOCUMENTS

| | | | | |
|---|---|---|---|---|
| 4,220,714 A | * | 9/1980 | Meiattini et al. | 435/17 |
| 4,877,579 A | * | 10/1989 | Yazawa et al. | 422/56 |
| 5,330,420 A | * | 7/1994 | Lee | 604/4 |
| 5,695,928 A | * | 12/1997 | Stewart | 435/5 |

OTHER PUBLICATIONS

Biological Abstracts 62035415 (1975), Le Gall et al, "Determination of phenotypes of red cell enzymes by electrophoresis on cellulose acetate."*
Biological Abstract 71059076 (1981), Bath et al, "Use of NAD-dependent glucose-6-phosphate dehydrogenase in enzyme staining procedures."*
Biological Abstract 91006139 (1991), Kurokawa et al, "Multiforms of mammalian adenylate kinase and its monoclonal antibody against AK,."*
Chemical Abstract 74(11): 50386 (1971), Alpen et al, "Thin layer starch gel electrophoresis for determining adenylate kinase types in blood stains."*
Chemical Abstract 78(13):82705 (1973), Mainzer et al. "Serum myokinase-(adenylate kinase) activity in intravascular hemolysis."*
Chemical Abstract 78(17):107073 (1973), MacGregor et al, "Molecular siwing of red cell membranes during gradual osmotic hemolysis."*

Chemical Abstract 98(15):122060 (1983), Malaya et al, "Determination of the adenylate kinase activity of the blood serum.".*
Beutler et al, "Metabolic Compensation for Profound Erythrocyte Adenylate Kinase Deficency" in J. Clin. Invest. 72(2):648-55, 1983.*
Koyama et al, "Antigenic Structure of Adenylate Kinase from Porcine Skeletal Muscle-II Immunochemical Crossreactivity . . . " Mol. Imm. 20(8) 851-856, 1983.*
Massey et al, "Crestine Kinase Isoenzymes in Nonate Plasma by Cellulose Acetate Electrophoresis : Albamin and Adenylate Kinase Artifacts," Clin Chem 28(5):1174-76, 1982.*
Matsuura et al, "Human Adenylate Kinase Deficiency Associated with Hemolytic Anemia," J. of Biol. Chem. 264(17) : 10148-55, 1989.*
Olchanes et al. "Yeast adenylate kinase . . . " FEBS Lett. 242(1) 187-193, Dec. 1988.*
Henry, J. (ed.) Clinical Diagnosis and Management by Laboratory Methods, 16th ed (W.B. Scundese Company 1979) pp 985-1032.*
E. Borglund et al., "Fluorometric Microassays of Adenylate Kinase . . . ," Upsale Journal of Medical Sciences, 83 : 81-84, 1978.*
T. Olsson et al., "Leakage of Adenylate Kinase from Stored Blood Cells," Journal of Applied Biochemistry, 5 : 437-445, 1983.*
C. Friedrich et al., "A General Method for Visualzing Enzymes Releasing Adenosine or Adenosine-5-Menophosphate," Biochemical Genetics 22: 389-394, 1984.*
J. Sock et al., "Activity Staining of Blotted Enzymes by Reaction Crapling with Transfer Membrane Immobalized Auxiliary Enzymes," Analytical Biochemistry 171: 310-319,1988.*
T. Tsuji et al., "Aprose thin-layer electrophoresis for the determination of red cell adenylate kinase (EC 2.7.4.3)," Chemical Abstract 86: 39099, 1977.*
Buth et al, "Use of NAD-dependent glucose-6-phosphate dehydrogenase in enzyme staining procedures," in Biological Abstracts, vol. 71 No. 9, Abstract # 59076 1981.*
Friedrich et al., "A General Method for Visualizing Enzyme Releasing Adenosine or Adenosine-5-Monophosphate, " Biochemical Genetics, vol. 22, Nos. 5/6 pp. 389-394 1984.*

(Continued)

*Primary Examiner*—Long V. Le
*Assistant Examiner*—Gailene R. Gabel
(74) *Attorney, Agent, or Firm*—Amster, Rothstein & Ebenstein LLP

(57) ABSTRACT

This invention provides a method for determining the presence of hemolyzed erythrocytes in blood by detecting erythrocyte adenylate kinase in a serum sample from the blood. This invention also provides a method for diagnosing a hemolytic condition in a subject suspected to be suffering from hemolysis, as well as a method for monitoring hemolysis in a subject undergoing treatment for a hemolytic condition.

9 Claims, 3 Drawing Sheets

OTHER PUBLICATIONS

Matsuura et al., "Human Adenylate Kinase Dificiency Associated with Hemolytic Anemia," The Journal of Biological Chemistry, vol. 264 No. 17, pp. 10148-10155 1989.*

Murthy, "Adenylate Kinase Mimics Crealine Kinase -MM Isoenzyme in a AK Isoenzyme Electrophoresis Assay," Journal of Clinical Laboratory Analysis, 8 : 140-143 1994.*

Olsson et al., "Leakage of Adenylate Kinase from Stored Blood Cells," Journal of Applied Biochemistry, vol. 5, pp 437-445 1983.*

Tsuji et al., "Agarose, thin-layer electrophoresis for the determination of red cell adenylate kinase (EC 2.7.4.3) polymorphisms," in Chemical Abstracts, vol 86, Abstract # 39099 1977.*

Szasz et al., "Creatine Kinase in Serum: 2. Interference of Adenylate Kinase with the Assay," Clinical Chemistry, 22(11) 1806-1811 Nov. 1976.*

Matsura et al. , Human Adenylate Kinase deficiency associated with Hemolytic Anemia, Journal of Biological Chemistry, 264 (17): 10148-10155 (1989)).*

Yeh et al., ATP-AMP phosphotransferase from Paracoccus denitrificans. European journal of biochemistry / FEBS, (Nov. 15, 1983) 136 (3) 523-9.*

Criss, Structural differences in the adenylate kinase enzymes. Enzyme, (1974) 18/5 (271-278).*

Koyama et al., Antigenic structure of adenylate kinase from porcine skeletal muscle--II. Immunochemical cross-reactivity of fragments from adenylate. Molecular immunology, (Aug. 1983) 20 (8) 851-6.*

Cruse et al., Illustrated Dictionary of Immunology, CRC Press, Inc. (1995), p. 274.*

Bais, R. and Edwards, J.B., *Pathology* 12:203-207 (1980).

Friedrich, C.A., et al., *Biochemical Genetics* 22:389-394 (1984).

Valentine, W.N., et al., *American Journal of Hematology* 32:143-145 (1989).

Murthy, V.V., *Journal of Clinical Laboratory Analysis* 8: 140-143 (1994).

Bijsterbosch, Martin K. et al., entitled "Several dehydrogenases and kinases compete for endocytosis from plasma by rat tissues," Biochem. J. (1985) 229, 409-417.

Fishbein, William N., et al., entitled "Indicator Enzyme Assays: II. Adenylate Kinase: Application to Human Muscle Biopsies and Blood Cells," Biochemical Medicine 24, 130-142 (1980).

Haslam, R.J. et al., entitled "The Adenylate Kinase of Human Plasma, Erythrocytes and Platelets in Relation to the Degradation of Adenosine Diphosphate in Plasma," Biochem. J. (1967) 103, 773-784.

Husic, David H., et al., entitled "The Levels of Creatine Kinase and Adenylate Kinase in the Plasma of Dystrophic Chickens Reflect the Rates of Loss of These Enzymes from the Circulation," Biochemical Medicine 29, 318-336 (1983).

Lindena J et al. Kinetic of Adjustment of Enzyme Catalytic Concentrations in the Extracellular Space of the Man, the Dog and the Rat: Approach to a Quantitative Diagnostic Enzymology V. Communication. J Clin Chem Clin Biochem 24: 61-71 1986.

Lindena J et al. The Decline of Catalyic Enzyme Activity Concentration of In Vivo Ageing Erythrocytes of the Man, the Dog and the Rat: Approach to Quantitative Diagnostic Enzymology, IV. Communication. J Clin Chem Clin Biochem 24: 49-59 1986.

Sashsenheimer, W., et al., entitled "Elimination und Exkretion von Adenylatkinasen nach Zellschadigungen," Klin. Wschr. 53, 617-622 (1975) Abstract Only.

Smit, Martin J. et al. Receptor-mediated Endocytosis of Lactate Dehydrogenase M4 by Liver Macrophages: a Mechanism for Elimination of Enzymes from Plasma, The Journal of Biological Chemistry, 262: 13020-6, 1987.

* cited by examiner

Linearity of Adenylate Kinase

METHOD FOR DETECTING HEMOLYSIS

This application is a continuation of U.S. application Ser. No. 08/421,079, filed Apr. 13, 1995, now abandoned.

BACKGROUND OF THE INVENTION

Anemia is a reduction in the normal levels of erythrocytes per cubic millimeter, the quantity of hemoglobin, or in the volume of packed red cells per one hundred milliliters. Although anemia is not a specific disease, it is the principal manifestation of a number of abnormal conditions such as deficiency conditions (caused by lack of iron, vitamin B12, or folic acid), hereditary disorders of the erythrocyte, disorders of the hematopoietic tissues (bone marrow damage or a hyperactive spleen) and gastrointestinal tract bleeding as a result of cancer or hemorrhage associated with organ trauma. As such, the diagnosis of the etiology of a patient's anemia is of great importance in enabling a treating physician to choose an appropriate therapeutic regimen.

Hemolysis is the disruption of the erythrocyte membrane causing release of hemoglobin and is one of the main causes of anemia. Hemolysis can occur as a result of a variety of factors, e.g. intracorpuscular hereditary defects within the erythrocyte triggered by extracellular factors such as drugs, plasma components, or splenic hyperactivity; or extracorpuscular factors such as infection, immunologic disease, and chemical or physical agents.

Anemia due to hemolysis is currently diagnosed by examination of a number of indirect markers. Findings of reticulocytosis (due to the increased efforts of the bone marrow to compensate for excessive erythrocyte destruction), increased erythrocyte fragility, shortened erythrocyte life span, hyperbilirubinemia, elevated serum levels of lactate dehydrogenase, increased fecal and urinary urobilinogen, or hemoglobinemia in cases of massive intravascular hemolysis, for example, will result in a diagnosis of hemolysis. However, use of such indirect indicators in the diagnosis of hemolysis is inaccurate. Very often, in patients who are suspected of suffering from hemolysis, the levels of the indirect markers are already altered as a result of concomitant disease. As a result, patient care is adversely affected because his or her therapy might be initiated or changed based upon misdiagnosis. Accordingly, there exists a need for an accurate and specific means for diagnosing hemolysis.

Adenylate kinases are a large family of enzymes found in plants, bacteria, and animals. The different members of the adenylate kinase family differ in composition, thermostability, optimum pH, substrate specificities, and kinetics. In humans, a variety of adenylate kinase isoenzymes, from a number of distinct sources, such as liver, intestine, muscle and erythrocytes, can be found in serum.

The inventors of the present invention have discovered that the level of erythrocyte adenylate kinase in serum correlates with the degree of hemolysis of blood. Based upon this discovery, the inventors of the present invention have devised an accurate method for detecting hemolysis in blood. Accordingly, the present invention satisfies the need for an accurate means for diagnosing hemolysis.

SUMMARY OF THE INVENTION

The present invention provides a method for detecting the presence of hemolyzed erythrocytes in blood comprising detecting erythrocyte adenylate kinase in a serum sample of said blood.

The present invention also provides a method for diagnosing a hemolytic condition in a subject suspected of having a hemolytic condition comprising collecting a serum sample from said subject, and detecting erythrocyte adenylate kinase in said serum sample.

Lastly, the present invention provides a method of monitoring the level of hemolysis in a patient which comprises measuring the erythrocyte adenylate kinase activity in a serum sample obtained from a patient being treated for hemolysis.

DETAILED DESCRIPTION OF THE INVENTION

Figure 1:
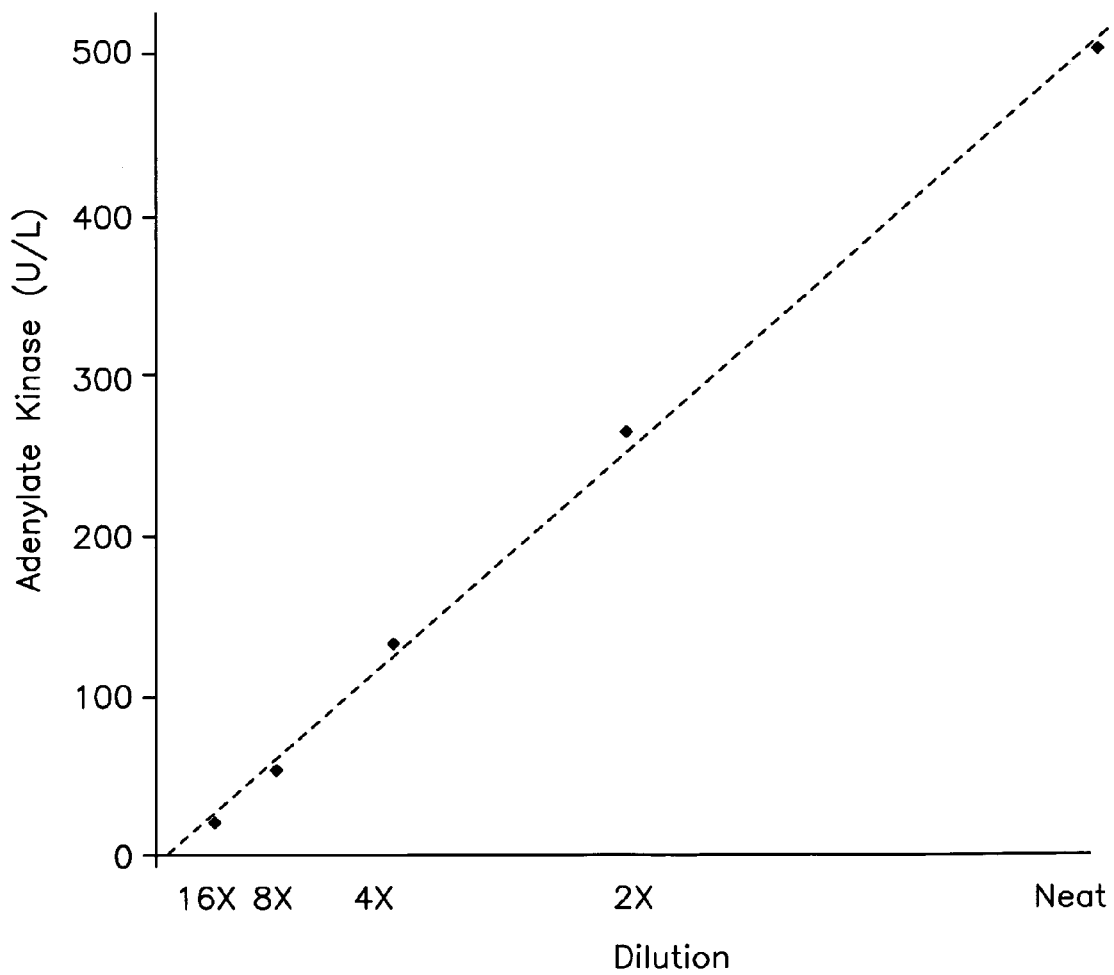
FIG. 1 represents a plot of adenylate kinase activity versus serial dilutions of a hemolyzed serum sample which exhibited high adenylate kinase activity. The serum sample was diluted using a solution of 9 g/L sodium chloride and the diluted solutions were assayed for adenylate kinase activity using a Cobas-FARA centrifugal analyzer.

The present invention provides a method for detecting the presence of hemolyzed erythrocytes in blood which comprises detecting erythrocyte adenylate kinase in a serum sample of the blood. The method of the present invention may be used to detect hemolysis in a subject suspected of having hemolysis. The subject may be animal or human, and preferably is human. The serum sample may be obtained by methods known in the art such as removal of blood by venipuncture followed by clotting (to remove fibrinogen) and slow speed centrifugation (2500 g) to remove particulate and cellular material followed by separation of the supernatant (serum) from the particulate and cellular material.

In one embodiment of the present invention, the erythrocyte adenylate kinase is detected by loading the serum sample onto an agarose gel of the type used to separate creatine kinase isoenzymes and electrophoresing the serum sample through the matrix of the gel. The erythrocyte adenylate kinase present in the serum sample migrates to a location on the gel matrix which corresponds to the MM isoenzyme of creatine kinase (Murthy, V. V. *Journal of Clinical Laboratory Analysis* 8:140–143 (1994)).

Upon completion of electrophoresis, the gel is submerged in an adenylate kinase-specific visualization reagent, preferably containing 12 mMol/L adenosine diphosphate, 60 mMol/L D-glucose, 6 mMol/L nicotinamide adenine dinucleotide, 9000 U/L hexokinase and 7500 U/L glucose-6-phosphate dehydrogenase. The combination of adenylate kinase in the gel and the adenylate kinase-specific visualization reagent initiates a coupled enzyme reaction which produces NADH (the reduced form of nicotinamide-adenine-dinucleotide) as an endproduct, as exemplified in the following reaction scheme:

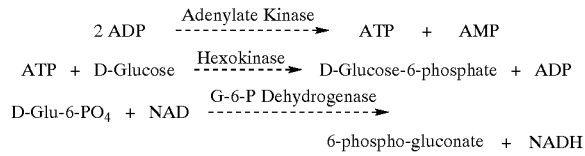

The endproduct, NADH, emits fluorescence upon exposure to ultraviolet light. The erythrocyte adenylate kinase is detected by the emission of fluorescent light from the location on the gel matrix to which the erythrocyte adenylate kinase migrates.

In another embodiment of the present invention, the presence of erythrocyte adenylate kinase in a serum sample is detected by contacting the serum sample with antibody against erythrocyte adenylate kinase and then detecting the complex formed between the erythrocyte adenylate kinase present in the serum sample and the erythrocyte adenylate kinase-specific antibody. The erythrocyte adenylate kinase-specific antibody can be monoclonal or polyclonal.

The antibodies against erythrocyte adenylate kinase must be raised against purified protein. Purification of erythrocyte adenylate kinase may be accomplished by fractionating hemolysates with ammonium sulfate, and fractionating the erythrocyte adenylate kinase using ion exchange chromatography or sephadex size exclusion chromatography.

Erythrocyte adenylate kinase can be used to make antibodies by methods well known in the art. The polyclonal antibody can be produced by immunizing a rabbit, mouse, or rat with the purified protein. If necessary, the protein may be attached to a carrier molecule (such as bovine serum albumin or keyhole limpet hemocyanin) in order to increase immunogenicity. After administration of a booster injection 4–6 weeks after the primary injection and additional boosters administered at later periods, if required, the presence of antibody is detectable by a variety of methods such as radioimmunoassay (RIA), enzyme-linked immunosorbent assay (ELISA) or immunoprecipitation.

Monoclonal antibodies can be produced by removing the spleen from the immunized rabbit, mouse or rat and fusing the spleen cells with myeloma cells to form a hybridoma. The hybridoma, when grown in culture, will produce a monoclonal antibody which can be detected and purified by RIA or ELISA.

In order to detect erythrocyte adenylate kinase by immunoprecipitation, a serum sample thought to contain erythrocyte adenylate kinase, is first mixed with antibody against erythrocyte adenylate kinase. The formation of a complex between antibody and erythrocyte adenylate kinase is then detected by sodium dodecyl sulfate (SDS) polyacrylamide electrophoresis (PAGE) (Davis, et.al., Basic Methods in Molecular Biology, 2nd. ed., (eds. Appleton & Lange), Section 17-2 (1994)).

The erythrocyte adenylate kinase in a serum sample may also be detected by Western blotting and immunodetection. A Western blot is prepared by the separation of the proteins in a serum sample thought to contain erythrocyte adenylate kinase by SDS PAGE; transferring the gel to a membrane (e.g. nitrocellulose); followed by incubating the membrane with primary antisera; and then detecting the presence of erythrocyte adenylate kinase using secondary antibody (Davis, et.al., supra).

In both immunoprecipitation, and Western blotting and immunodetection, detection of complexes between antibody and target can be accomplished by isotopic or nonisotopic means, i.e. the erythrocyte adenylate kinase antibody (immunoprecipitation) or secondary antiserum (Western blotting) can be labeled with a radioisotope such as radioactive iodine, and complex formation detected by autoradiography of the gel or membrane; alternatively, the erythrocyte adenylate kinase antibody or secondary antiserum can be labeled with nonisotopic means, e.g. it can be conjugated to horseradish peroxidase or alkaline phosphatase and complex formation detected by a visible color change and conventional autoradiography, respectively (Davis, et.al., supra).

Detection of erythrocyte adenylate kinase by immunoelectrophoresis can be accomplished by electrophoresing the serum sample through a gel matrix such as agarose and then placing erythrocyte adenylate kinase antibody in a trough which is cut parallel to the direction of electrophoresis. The antibodies are allowed to diffuse through the gel—the proteins diffusing radially from their electrophoretic placement and the antibodies diffusing perpendicularly from the trough. If erythrocyte adenylate kinase is present in the serum sample, it will be detected by the formation of an elliptical precipitin arc (Davis, et.al. Microbiology, 4th. ed., pp. 274–275 (1990)).

The present invention also provides a method for monitoring hemolysis in a subject being treated for an hemolysis-related condition such as hemolytic anemia, by measuring and quantifying the erythrocyte adenylate kinase activity in the serum sample. The method comprises the steps of first determining the total adenylate kinase activity in the serum sample; then calculating the percentage erythrocyte adenylate kinase in the sample; and finally calculating the total erythrocyte adenylate kinase activity in the sample by multiplying the value for percentage erythrocyte adenylate kinase by the value for total adenylate kinase activity.

Total adenylate kinase activity is determined by mixing the serum sample with an adenylate kinase-specific visualization reagent (described above) and then analyzing the mixture in a Cobas-FARA centrifugal analyzer (from Roche Diagnostics, Branchburg, N.J.). Total adenylate kinase activity is calculated by measuring the formation of the NADH end product of the already described coupled enzyme reaction (formation of NADH is measured from the change in absorbance of the mixture over time). One unit of adenylate kinase is equal to one micromole of product (NADH) formed per minute.

The percentage of erythrocyte adenylate kinase in the serum sample is measured by electrophoresing the serum sample on an agarose gel of the type used to separate creatine kinase isoenzymes, staining the gel with an adenylate kinase-specific visualization reagent (described above) and irradiating the gel with ultraviolet light. Measurement of total fluorescence from the gel provides a value for the total amount of adenylate kinase present; measurement of fluorescence from the location of the gel at which erythrocyte adenylate kinase migrates, provides a value for the amount of erythrocyte adenylate kinase present in the serum sample. The percentage of erythrocyte adenylate kinase in the sample is calculated by dividing the value for erythrocyte adenylate kinase by the value for adenylate kinase. The erythrocyte adenylate kinase activity in the serum sample is calculated by multiplying the percentage of erythrocyte adenylate kinase by the adenylate kinase activity.

Alternatively, erythrocyte adenylate kinase activity can be quantitated using the monoclonal or polyclonal antibodies described above. In order to quantitate the activity of erythrocyte adenylate kinase present in a serum sample, RIA or ELISA can be used. Another suitable method involves immunoprecipitation in solution followed by measuring the development of turbidity using a turbidometer or nephelometer.

For RIA, a known concentration of radioactively labeled erythrocyte adenylate kinase is added to the serum sample together with antibody. The level of binding between antibody and labeled erythrocyte adenylate kinase is used as a measure of the activity of erythrocyte adenylate kinase present in the serum sample by reference to calibration curves prepared using purified erythrocyte adenylate kinase of known activity (Davis, et.al. Microbiology, 4th. ed., pp. 267–268 (1990)).

For ELISA, erythrocyte adenylate kinase antibody (antibody 1) is bound to a solid surface, e.g. plastic beads or tray. The bound antibody is then mixed with a serum sample thought to contain erythrocyte adenylate kinase. A second erythrocyte adenylate kinase antibody (antibody 2) is then added to the mixture. Antibodies 1 and 2 recognize different regions of the erythrocyte adenylate kinase molecule and so both can bind in a non-exclusive manner. A third antibody (antibody 3), which reacts with antibody 2, but not antibody 1 is then added. Antibody 3 is conjugated to an enzyme and it is the action of this enzyme which provides the basis for detection. A variety of enzymes can be used in ELISAs, e.g. alkaline phosphatase, horseradish peroxidase, or beta-galactosidase. No matter the enzyme used for detection, quantitation of erythrocyte adenylate kinase activity in the serum sample is measured both accurately and rapidly using calibrated, automated ELISA reader devices (Davis, et.al. Microbiology, 4th. ed., pp. 269–270 (1990)).

The present invention is described in the following Experimental Details section, which sets forth a specific example to aid in the understanding of the invention, and should not be construed to limit, in any way, the invention as defined in the claims which follow thereafter.

Experimental Details Section

A. Materials and Methods

1. Electrophoresis

The Helena REP creatine kinase electrophoresis apparatus was used to fractionate the erythrocyte adenylate kinase in serum samples. Agarose gels used for fractionating creatine kinase in the REP creatine kinase system were purchased from Helena Laboratories, Beaumont, Tex. All other reagents were purchased from Sigma, St. Louis, Mo.

2. Assays

The adenylate kinase specific visualization reagent used to visualize adenylate kinase on the gel contained: 12 mMol/L adenosine diphosphate, 60 mMol/L each of D-glucose and magnesium acetate, 6 mMol/L nicotinamide adenine dinucleotide, 9000 U/L of hexokinase and 7500 U/L of glucose-6-phosphate dehydrogenase in 100 mMol/L Tris buffer, pH 8.0. Adenylate kinase activity on the gel was visualized as a 360 nm fluorescence spot of the NADH product of the coupled enzyme reaction described above.

Total adenylate kinase activity in serum was measured using a Cobas-Fara centrifugal analyzer (from Roche Diagnostics, Branchburg, N.J.) and a ten fold dilution of the adenylate kinase visualization reagent described above.

The relative percentage of erythrocyte adenylate kinase present in the serum sample was determined from the fluorescence associated with the known location of the erythrocyte adenylate kinase on the gel. The erythrocyte adenylate kinase activity was calculated by multiplying the percentage of erythrocyte adenylate kinase present in the serum sample by the total adenylate kinase activity.

The amount of hemolysis was estimated by measuring serum hemoglobin concentration using a Coulter STKS instrument (Coulter Corporation, Hialeah, Fla.).

3. Serum Samples

Serum samples were obtained from 20 patients suspected of having hemolysis and analyzed. Fifteen out of the 20 samples exhibited various degrees of red pigmentation upon visual inspection. The remaining 5 samples did not show any obvious hemolysis.

Freshly collected blood from a volunteer was used to obtain an erythrocyte hemolysate. Serial dilutions of the hemolysate were made with a hypotonic solution containing sodium chloride prior to assaying the samples for adenylate kinase.

B. Results

The assay for total adenylate kinase was found to be linear up to 500 U/L, when a serially diluted freshly prepared erythrocyte hemolysate was used as the source of adenylate kinase (see FIG. 1). The total adenylate kinase activity in the serum samples analyzed ranged from 5 to 464 U/L as shown in Table 1. Results from duplicate assays showed a high degree of reproducability.

Figure 2:
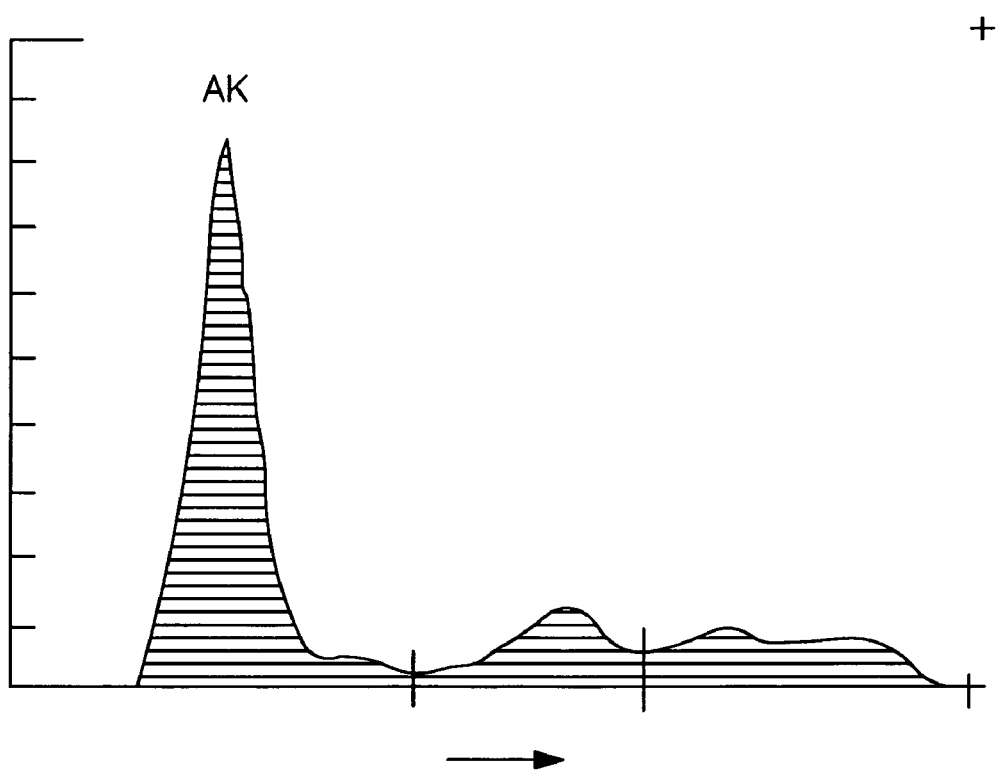
FIG. 2 represents a scan of adenylate kinase isoenzyme activities after electrophoretic resolution of a hemolyzed serum sample (2 g/L hemoglobin) containing 87 U/L of adenylate kinase activity. The serum sample was subjected to adenylate kinase isoenzyme electrophoretic fractionation on an agarose gel with the Helena REP system. The direction of migration is from left to right (anode is to the right). The slow moving fluorescent band migrating near the cathode represents erythrocyte adenylate kinase isoenzyme activity.

The serum samples with measurable total adenylate kinase activity were electrophoresed in the REP creatine kinase instrument using the agarose gels routinely employed for creatine kinase fractionation. Adenylate kinase was visualized using the adenylate kinase-specific visualization reagent. All 15 samples which exhibited hemolysis on visual inspection, showed elevated erythrocyte adenylate kinase activity. A representative scan of erythrocyte adenylate kinase activity is shown in FIG. 2. Erythrocyte adenylate kinase activity was not detected in the 5 serum samples which were not hemolyzed on visual inspection.

Figure 3:
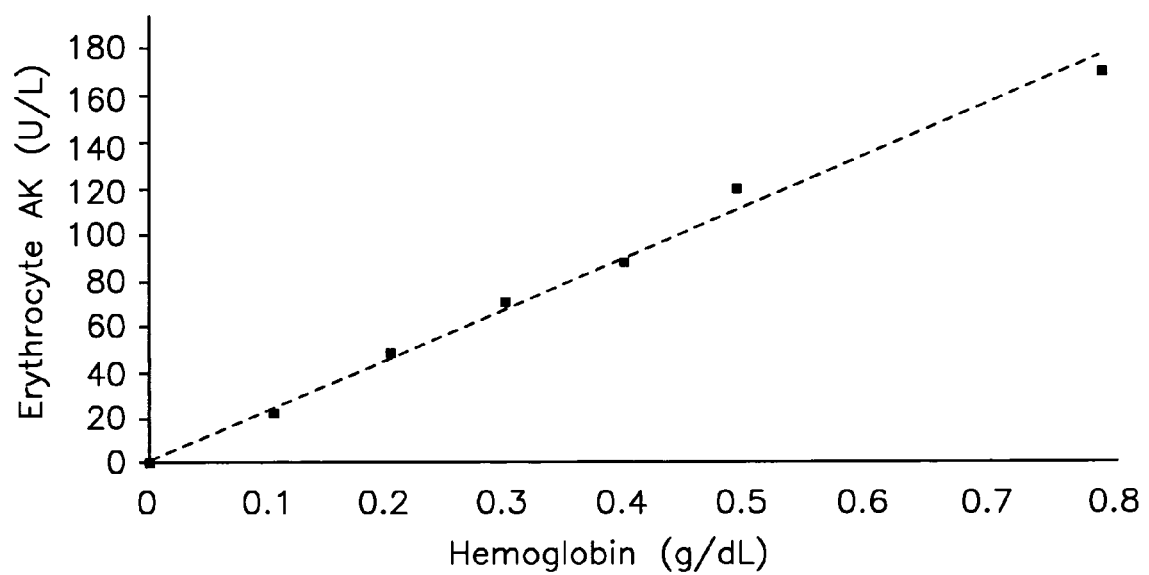
FIG. 3 represents a plot of erythrocyte adenylate kinase activity versus hemoglobin concentration in hemolyzed samples. Erythrocyte adenylate kinase activity (U/L) was calculated by multiplying total adenylate kinase in each sample (determined using the Cobas-FARA centrifugal analyzer) by the percentage erythrocyte adenylate kinase (determined from the REP electrophoresis assay) in the sample. The same samples were also assayed for hemoglobin concentration with the Coulter STKS analyzer. Results are of duplicate assays.

The erythrocyte adenylate kinase activity, measured using the REP electrophoresis assay, was found to be linear between the ranges of 0–120 U/L and was proportional to hemoglobin concentrations between 0 and 5 g/L as shown in FIG. 3. About 1 U/L erythrocyte adenylate kinase activity is equal to about 0.005 g/DL hemoglobin concentration.

All publications mentioned herein above are hereby incorporated in their entirety.

While the foregoing invention has been described in some detail for the purposes of clarity and understanding, it will be appreciated by one skilled in the art from a reading of the disclosure that various changes in form and detail can be made without departing from the true scope of the invention in the appended claims.

TABLE 1

Effect of Hemolysis on Adenylate Kinase Activity in Serum

| SAMPLE NUMBER | HEMOGLOBIN (g/L) | ADENYLATE KINASE (U/L) | |
|---|---|---|---|
| | | Run 1 | Run 2 |
| 1 | 1.0 | 21 | 22 |
| 2 | 1.0 | 48 | 48 |
| 3 | 1.0 | 21 | 21 |
| 4 | 2.0 | 45 | 44 |
| 5 | 2.0 | 48 | 48 |
| 6 | 2.0 | 58 | 56 |
| 7 | 2.0 | 53 | 53 |
| 8 | 2.0 | 64 | 63 |
| 9 | 2.0 | 88 | 86 |
| 10 | 2.0 | 157 | 150 |
| 11 | 3.0 | 82 | 85 |
| 12 | 3.0 | 172 | 165 |
| 13 | 5.0 | 153 | 147 |
| 14 | 5.0 | 472 | 454 |
| 15 | 6.0 | 194 | 187 |
| 16 | 0 | 1 | 0* |
| 17 | 0 | 5 | 5* |
| 18 | 0 | 5 | 5* |
| 19 | 0 | 11 | 11* |
| 20 | 0 | 32 | 32* |

*Samples 1–15 were hemolyzed; samples 16–20 were not.

What is claimed is:

1. A method for diagnosing erythrocyte hemolysis in a subject who is suspected of having erythrocyte hemolysis in vivo, the method consiting essentially of the steps of:
   (a) obtaining a serum sample from a subject who is suspected of having erythrocyte hemolysis in vivo; and
   (b) determining the level of erythrocyte adenylate kinase activity in said sample, the presence of at least about 20 U/L erythrocyte adenylate kinase activity in said sample being indicative of erythrocyte hemolysis in vivo in said subject.

2. A method for diagnosing erythrocyte hemolysis in a subject who may have erythrocyte hemolysis, the method comprising the steps of:
   (a) obtaining a serum sample from the subject; and
   (b) determining the level of erythrocyte adenylate kinase activity in the sample by
      determining a value for total adenylate kinase activity in the serum sample;
      determining a value for percentage erythrocyte adenylate kinase in the sample; and
      determining erythrocyte adenylate kinase activity in the sample by multiplying the value for percentage erythrocyte adenylate kinase by the value for total adenylate kinase activity,
   the presence of at least about 20 U/L erythrocyte adenylate kinase activity in the sample being indicative of erythrocyte hemolysis in the subject.

3. A method for diagnosing erythrocyte hemolysis in a subject who may have erythrocyte hemolysis, the method comprising the steps of:
   (a) obtaining a serum sample from the subject; and
   (b) determining the level of erythrocyte adenylate kinase activity in the sample using an antibody that is specific for and binds to erythrocyte adenylate kinase,
   the presence of at least about 20 U/L erythrocyte adenylate kinase activity in the sample being indicative of erythrocyte hemolysis in the subject.

4. The method of claim 3, wherein erythrocyte adenylate kinase-bound antibody is detected using a radioimmunoassay.

5. The method of claim 3, wherein erythrocyte adenylate kinase-bound antibody is detected using an enzyme-linked immunosorbent assay (ELISA).

6. The method of claim 3, wherein erythrocyte adenylate kinase-bound antibody is detected using immunoprecipitation.

7. The method of claim 3, wherein the antibody is labeled with a detectable marker.

8. The method of claim 3, wherein the antibody is labeled with a radioisotope.

9. The method of claim 3, wherein the antibody is labeled with radioactive iodine.

* * * * *